(12) United States Patent
Konetzki et al.

(10) Patent No.: US 7,423,036 B2
(45) Date of Patent: Sep. 9, 2008

(54) LONG-ACTING BETAMIMETICS FOR THE TREATMENT OF RESPIRATORY COMPLAINTS

(75) Inventors: Ingo Konetzki, Warthausen (DE); Christoph Hoenke, Ingelheim (DE); Thierry Bouyssou, Birkenhard (DE); Andreas Schnapp, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 10 days.

(21) Appl. No.: 11/355,065

(22) Filed: Feb. 15, 2006

(65) Prior Publication Data

US 2006/0189607 A1 Aug. 24, 2006

(30) Foreign Application Priority Data

Feb. 19, 2005 (DE) ........................ 10 2005 007 654

(51) Int. Cl.
*C07D 413/02* (2006.01)
*C07D 403/02* (2006.01)
*A61K 31/538* (2006.01)
*A61K 31/4709* (2006.01)

(52) U.S. Cl. .................... 514/230.5; 514/312; 514/376; 544/105; 546/158; 548/221

(58) Field of Classification Search ................. 544/105; 514/230.5, 312, 376; 546/158; 548/221
See application file for complete search history.

(56) References Cited

U.S. PATENT DOCUMENTS

| 4,154,829 | A | 5/1979 | Mentrup et al. |
| 4,460,581 | A | 7/1984 | Schromm et al. |
| 7,056,916 | B2 | 6/2006 | Konetzki et al. |
| 2002/0022625 | A1 | 2/2002 | Walland et al. |
| 2005/0197374 | A1 | 9/2005 | Bouyssou et al. |
| 2005/0256114 | A1 | 11/2005 | Grauert et al. |

FOREIGN PATENT DOCUMENTS

| CA | 2 405 745 A1 | 11/2001 |
| CA | 2 506 082 A1 | 6/2004 |
| CA | 2 552 871 A1 | 8/2005 |
| CA | 2 562 859 A1 | 11/2005 |
| WO | 01/83462 A1 | 11/2001 |
| WO | WO 2004/045618 A2 | 6/2004 |
| WO | WO 2005/077361 A1 | 8/2005 |
| WO | WO 2005/111004 A1 | 11/2005 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
International Search Report dated Jul. 25, 2006—PCT/EP2006/050898.

* cited by examiner

*Primary Examiner*—Kahsay T Habte
(74) *Attorney, Agent, or Firm*—Michael P. Morris; Edouard G. Lebel; Mary-Ellen M. Devlin

(57) ABSTRACT

The present invention relates to compounds of formula 1, wherein n, A, $R^1$, $R^2$ and $R^3$ may have the meanings specified in the description and claims, processes for preparing them and their use as pharmaceutical compositions, particularly as pharmaceutical compositions for the treatment of respiratory complaints.

20 Claims, No Drawings

LONG-ACTING BETAMIMETICS FOR THE TREATMENT OF RESPIRATORY COMPLAINTS

This application claims priority to German Application 10 2005 007 654, filed on Feb. 19, 2005, which is incorporated herein in its entirety.

The present invention relates to compounds of formula 1,

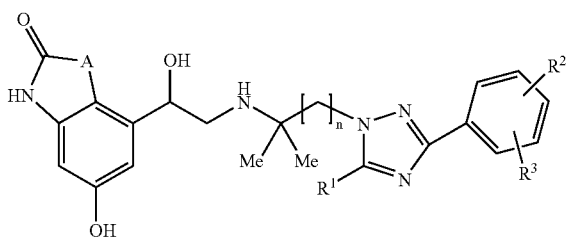

wherein n, A, $R^1$, $R^2$ and $R^3$ may have the meanings specified in the description and claims, processes for preparing them and their use as pharmaceutical compositions, particularly as pharmaceutical compositions for the treatment of respiratory complaints.

BACKGROUND TO THE INVENTION

Betamimetics (β-adrenergic substances) are known from the prior art. For example, reference is made in this respect to the disclosure of WO 04/045618, WO 01/83462 but also older publications, such as for example U.S. Pat. No. 4,460,581 or U.S. Pat. No. 4,154,829. These propose betamimetics for the treatment of a number of ailments.

Basically, in the drug treatment of a number of diseases, it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance over longer time intervals contributes to the well-being of the patient to a high degree.

It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to prepare betamimetics which on the one hand provide a therapeutic benefit in the treatment of respiratory complaints and are also characterised by a longer duration of activity and can thus be used to prepare pharmaceutical compositions with a longer duration of activity. A particular aim of the invention is to prepare betamimetics which, by virtue of their long-lasting effect, can be used to prepare a drug for the treatment of respiratory complaints for administration once a day. In addition to these aims, a further objective of the invention is to provide such betamimetics which are not only exceptionally potent but are also characterised by a high degree of selectivity with respect to the $\beta_2$-adreno-receptor.

DESCRIPTION OF THE INVENTION

Surprisingly it has been found that the abovementioned problems are solved by compounds of formula 1.

Accordingly, the present invention relates to compounds of formula 1,

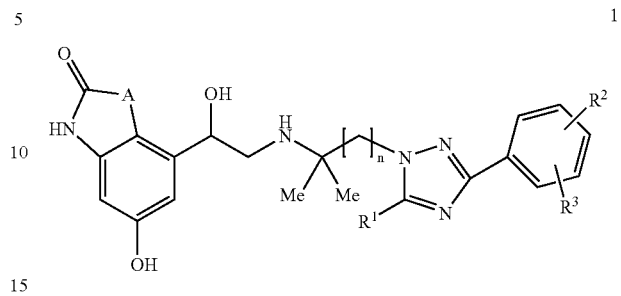

wherein
n denotes 1, 2, 3 or 4;
A denotes a double-bonded group selected from among —O—, —$CR^4R^5$—, —$NR^6$—, —S—, —$CR^4R^5$—O—, —$CR^4R^5$—$NR^6$—, —CH═CH— or —$CH_2$-$CH_2$—;
$R^1$ denotes —$C_{1-6}$-alkyl;
$R^2$ and $R^3$, which may be identical or different, denote H, $C_{1-6}$-alkyl, $C_{2-6}$-alkenyl, $C_{2-6}$-alkynyl, $C_{3-6}$-cycloalkyl, $C_{1-6}$-haloalkyl, —O—$C_{1-6}$-haloalkyl, halogen, OH, CN, $NO_2$, O—$C_{1-6}$-alkyl, —$C_{2-6}$-alkyl-OH, $NH_2$, NH—$C_{1-6}$-alkyl, N($C_{1-6}$-alkyl)$_2$, NHCO—$C_{1-6}$-alkyl, $NHSO_2$—$C_{1-6}$-alkyl, S—$C_{1-6}$-alkyl, SO—$C_{1-6}$-alkyl, $SO_2$-$C_{1-6}$-alkyl, $SO_2NH_2$, $SO_2NH$—$C_{1-6}$-alkyl, $SO_2N(C_{1-6}$-alkyl)$_2$, $CONH_2$, CONH—$C_{1-6}$-alkyl, CON($C_{1-6}$-alkyl)$_2$, —CO—$C_{1-6}$-alkyl, COOH or COO—$C_{1-4}$-alkyl, or
$R^2$ and $R^3$ together denote a double-bonded group selected from —O—$CR^4R^5$—O—, —O—$CR^4R^5$—$NR^6$— or —CH═CH—CH═CH—;
$R^4$ denotes H or $C_{1-6}$-alkyl;
$R^5$ denotes H or $C_{1-6}$-alkyl;
$R^6$ denotes H or $C_{1-6}$-alkyl, optionally in the form of the individual enantiomers, mixtures of the individual enantiomers or racemates, optionally in the form of the pharmacologically acceptable acid addition salts thereof, and optionally in the form of the solvates and/or hydrates thereof.

Preferred compounds of formula 1 above are those wherein
n denotes 1, 2 or 3, preferably 2;
A denotes a double-bonded group selected from among —$CR^4R^5$—O—, —CH═CH— or —$CH_2$—$CH_2$—, preferably —$CR^4R^5$—O—;
$R^1$ denotes —$C_{1-4}$-alkyl;
$R^2$ and $R^3$, which may be identical or different, denote H, $C_{104}$-alkyl, $C_{2-4}$-alkenyl, $C_{2-4}$-alkynyl, $C_{3-6}$-cycloalkyl, $C_{1-4}$-haloalkyl, —O—$C_{1-4}$-haloalkyl, halogen, OH, CN, $NO_2$, —$C_{2-4}$-alkyl-OH, —O—$C_{1-4}$-alkyl, COOH or COO—$C_{1-4}$-alkyl, or
$R^2$ and $R^3$ together denote a double-bonded group selected from —O—$CR^4R^5$—O—, —O—$CR^4R^5$—$NR^6$— or —CH═CH—CH═CH—;
$R^4$ denotes H or $C_{1-4}$-alkyl;
$R^5$ denotes H or $C_{1-4}$-alkyl;
$R^6$ denotes H or $C_{1-4}$-alkyl, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Also preferred are the compounds of formula 1, wherein
A denotes a double-bonded group selected from among —$CR^4R^5$—O, —CH=CH or —$CH_2$—$CH_2$, preferably —$CR^4R^5$—O— where
$R^4$ denotes H, methyl, ethyl, preferably H or methyl, particularly preferably H;
$R^5$ denotes H, methyl, ethyl, preferably H or methyl, particularly preferably H;

and wherein n, $R^1$, $R^2$, $R^3$ and $R^6$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Also preferred are the compounds of formula 1, wherein
$R^1$ denotes methyl, ethyl or propyl, preferably methyl or ethyl, particularly preferably methyl and wherein n, A, $R^2$, $R^3$, $R^4$, $R^5$ and $R^6$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Also preferred are compounds of formula 1, wherein
$R^2$ denotes H, methyl, ethyl, propyl, vinyl, allyl, propargyl, cyclopropyl, cyclopentyl, cyclohexyl, —$CH_2Cl$, —$CHCl_2$, —$CCl_3$, —$CH_2F$, —$CHF_2$, —$CF_3$, —$CH_2$—$CH_2Cl$, —$CH_2$—$CHCl_2$, —$CH_2$—$CCl_3$, —$CH_2$—$CH_2F$, —$CH_2$—$CHF_2$, —$CH_2$—$CF_3$, —$CH_2$—$CH_2OH$ fluorine, chlorine, bromine, OH, CN, $NO_2$, methoxy, ethoxy, propoxy, COOH, COO-methyl, COO-ethyl, COO-propyl or COO-butyl;
$R^3$ denotes methyl, ethyl, propyl, vinyl, allyl, propargyl, cyclopropyl, cyclopentyl, cyclohexyl, —$CH_2Cl$, —$CHCl_2$, —$CCl_3$, —$CH_2F$, —$CHF_2$, —$CF_3$, —$CH_2$—$CH_2Cl$, —$CH_2$—$CHCl_2$, —$CH_2$—$CCl_3$, —$CH_2$—$CH_2F$, —$CH_2$—$CHF_2$, —$CH_2$—$CF_3$, —$CH_2$—$CH_2OH$, fluorine, chlorine, bromine, OH, CN, $NO_2$, methoxy, ethoxy, propoxy, COOH, COO-methyl, COO-ethyl, COO-propyl or COO-butyl, or
$R^2$ and $R^3$ together denote a double-bonded group selected from —O—$CR^4R^5$—O, —O—$CR^4R^5$—$NR^6$ or —CH=CH—CH=CH—;
$R^4$ denotes H, methyl, ethyl, preferably H or methyl, particularly preferably H;
$R^5$ denotes H, methyl, ethyl, preferably H or methyl, particularly preferably H;
$R^6$ denotes H, methyl, ethyl, preferably H or methyl, particularly preferably H;

and wherein n, A and $R^1$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Also preferred are compounds of formula 1, wherein
$R^2$ denotes H, methyl, ethyl, —$CF_3$, —$CH_2$—$CF_3$, fluorine, chlorine, OH, methoxy, ethoxy, COOH or COO-methyl;
$R^3$ denotes methyl, ethyl, propyl, vinyl, allyl, cyclopropyl, cyclopentyl, cyclohexyl, —$CH_2F$, —$CHF_2$, —$CF_3$, —$CH_2$—$CH_2F$, —$CH_2$—$CHF_2$, —$CH_2$—$CF_3$, —$CH_2CH_2OH$, fluorine, chlorine, OH, CN, methoxy, ethoxy, COOH, COO-methyl, COO-ethyl or COO-butyl, or
$R^2$ and $R^3$ together denote a double-bonded group selected from —O—$CH_2$—O, —O—$CMe_2$—O or —CH=CH—CH=CH—;

and wherein n, A and $R^1$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Also preferred are compounds of formula 1, wherein
$R^2$ denotes H, methyl, ethyl, —$CF_3$, fluorine, chlorine, OH or methoxy;
$R^3$ denotes methyl, ethyl, cyclopropyl, cyclohexyl, —$CF_3$, fluorine, chlorine, OH, CN, methoxy, ethoxy, COOH, COO-methyl, COO-ethyl or COO-butyl, or
$R^2$ and $R^3$ together denote a double-bonded group selected from —O—$CH_2$—O— or —CH=CH—CH=CH—;

and wherein n, A and $R^1$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Also preferred are compounds of formula 1, wherein
$R^2$ denotes H, methyl, fluorine, chlorine, OH or methoxy;
$R^3$ denotes methyl, ethyl, —$CF_3$, fluorine, chlorine, OH, methoxy, ethoxy, COOH, COO-methyl or COO-butyl, or
$R^2$ and $R^3$ together denote a double-bonded group selected from —O—$CH_2$—O— or —CH=CH—CH=CH, preferably —O—$CH_2$—O—;

and wherein n, A and $R^1$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Also preferred are compounds of formula 1, wherein $R^2$ denotes hydrogen and wherein n, A, $R^1$ and $R^3$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Also preferred are compounds of formula 1, wherein n denotes 2 and wherein A, $R^1$, $R^2$ and $R^3$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Also preferred are compounds of formula 1, wherein
$R^3$ denotes methyl, ethyl, —$CF_3$, fluorine, chlorine, OH, methoxy, ethoxy, COOH, COO-methyl or COO-butyl, preferably methyl, —$CF_3$, fluorine, chlorine, OH, methoxy, COOH or COO-methyl, particularly preferably methyl, -$CF_3$, fluorine, chlorine, methoxy or COOH, and wherein n, A, $R^1$ and $R^2$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

In another aspect the present invention relates to the abovementioned new compounds of formula 1 in the form of the individual optical isomers, mixtures of the individual enantiomers or racemates. Particularly preferred are compounds of formula 1 in the form of the enantiomerically pure compounds, while the R-enantiomers of the compounds of formula 1 according to the invention are of exceptional importance. The R-enantiomers of the compounds of formula 1 may be represented by general formula R-1

R-1

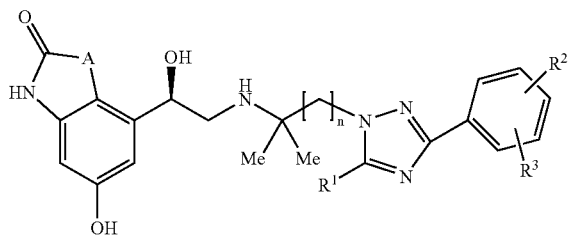

wherein n, A, $R^1$, $R^2$ and $R^3$ may have the above-mentioned meanings.

Methods of separating racemates into their respective enantiomers are known in the prior art and may be used analogously to prepare the enantiomerically pure R- or S-enantiomers of the compounds of formula 1.

Also preferred are compounds of formula 1, wherein A denotes —$CH_2$—O— and wherein the groups n, $R^1$, $R^2$ and $R^3$ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof. Of the compounds of formula 1 wherein A denotes —$CH_2$—O—, preferred regioisomers are those which are characterised by general formula 1.1.

1.1

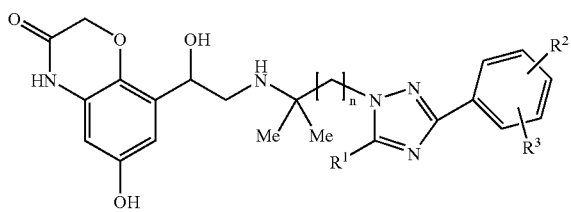

In a preferred aspect the present invention relates to compounds of formula 1.1 wherein n, $R^1$, $R^2$ and $R^3$ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof. Particularly preferred according to the invention are the R-enantiomers of the compounds of formula 1.1.

Compounds of Formula 1 Wherein A Denotes CH═CH are Characterised by General Formula 1.2.

1.2

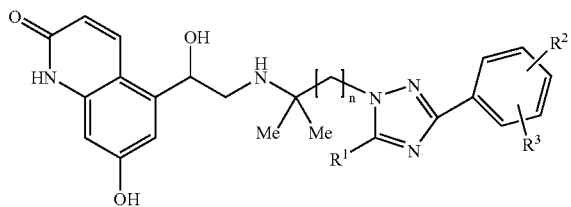

In a preferred aspect the present invention relates to compounds of formula 1.2 wherein n, $R^1$, $R^2$ and $R^3$ may have the above-mentioned meanings, optionally in the form of the individual enantiomers, mixtures of the individual enantiomers or racemates, optionally in the form of the acid addition salts thereof with pharmacologically acceptable acids as well as optionally in the form of the solvates and/or hydrates thereof. Particularly preferred according to the invention are the R-enantiomers of the compounds of formula 1.2.

Compounds of Formula 1 Wherein A Denotes $CH_2$—$CH_2$ are Characterised by General Formula 1.3.

1.3

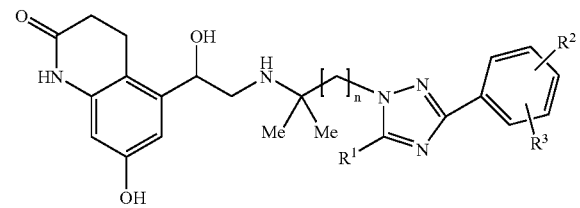

In a preferred aspect the present invention relates to compounds of formula 1.3 wherein n, $R^1$, $R^2$ and R may have the above-mentioned meanings, optionally in the form of the individual enantiomers, mixtures of the individual enantiomers or racemates, optionally in the form of the acid addition salts thereof with pharmacologically acceptable acids as well as optionally in the form of the solvates and/or hydrates thereof. Particularly preferred according to the invention are the R-enantiomers of the compounds of formula 1.3.

Compounds of formula 1 wherein A denotes —$CR^4R^5$—O— and $R^4$ or $R^5$ denotes methyl are also preferred according to the invention. Particularly preferred regioisomers of this structural category are characterised by general formula 1.4.

1.4

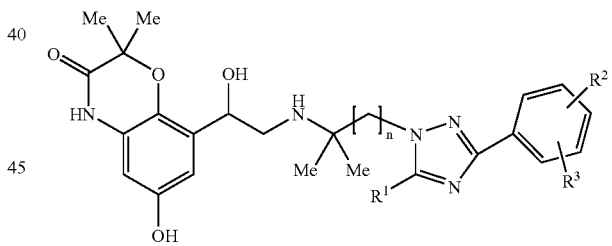

In a preferred aspect the present invention relates to compounds of formula 1.4 wherein n, $R^1$, $R^2$ and $R^3$ may have the above-mentioned meanings, optionally in the form of the individual enantiomers, mixtures of the individual enantiomers or racemates, optionally in the form of the acid addition salts thereof with pharmacologically acceptable acids as well as optionally in the form of the solvates and/or hydrates thereof. Particularly preferred according to the invention are the R-enantiomers of the compounds of formula 1.4.

Also preferred are compounds of formula 1 wherein A denotes a double-bonded group selected from among —O, —$CR^4R^5$ or —$NR^6$— and wherein n, $R^1$, $R^2$, $R^3$, $R^4$, $R^5$ and $R^6$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Also preferred are compounds of formula 1 wherein A denotes a double-bonded group —S— and wherein n, $R^1$, $R^2$, and $R^3$ may each have one of the meanings given above or hereinafter, optionally in the form of the individual enantiomers, mixtures of the individual enantiomers or racemates, optionally in the form of the pharmacologically acceptable acid addition salts thereof, as well as optionally in the form of the solvates and/or hydrates thereof.

Particularly preferred are compounds of formula 1 which are selected from the group of compounds consisting of:
- 8-(2-{3-[3-(4-fluoro-phenyl)-5-methyl-[1,2,4]triazol-1-yl]-1,1-dimethyl-propylamino}-1-hydroxy-ethyl)-6-hydroxy-4h-benzo[1,4]oxazin-3-one;
- 8-{2-[1,1-dimethyl-3-(5-methyl-3-p-tolyl-[1,2,4]triazol-1-yl)-propylamino]-1-hydroxy-ethyl{-6-hydroxy-4H-benzo[1,4]oxazin-3-one;
- 8-(2-{1,1-dimethyl-3-[5-methyl-3-(4-trifluoromethyl-phenyl)-[1,2,4]triazol-1-yl]-propylamino}-1-hydroxy-ethyl)-6-hydroxy-4H-benzo[1,4]oxazin-3-one;
- 8-(2-{3-[3-(3,5-difluoro-phenyl)-5-methyl-[1,2,4]triazol-1-yl]-1,1-dimethyyl-propylamino}-1-hydroxy-ethyl)-6-hydroxy-4H-benzo[1,4]oxazin-3-one;
- 3-(1-{3-[2-hydroxy-2-(6-hydroxy-3-oxo-3,4-dihydro-2H-benzo[1,4]oxazin-8-yl)-ethylamino]-3-methyl-butyl}-5-methyl-1H-[1,2,4]triazol-3-benzoic acid;
- 8-(2-{3-[3-(4-chloro-phenyl)-5-methyl-[1,2,4]triazol-1-yl]-1,1-dimethyl-propylamino}-1-hydroxy-ethyl)-6-hydroxy-4H-benzo[1,4]oxazin-3-one;
- 8-(2-{3-[5-ethyl-3-(4-methoxy-phenyl)-[1,2,4]triazol-1-yl]-1,1-dimethyl-propylamino}-1-hydroxy-ethyl)-6-hydroxy-4H-benzo[1,4]oxazin-3-one;
- 6-hydroxy-8-(1-hydroxy-2-{3-[3-(4-methoxy-phenyl)-5-methyl-[1,2,4]triazol-1-yl]-1,1-dimethyl-propylamino{-ethyl)-4H-benzo[1,4]oxazin-3-one;
- 8-{2-[3-(3-benzo[1,3]dioxol-5-yl-5-methyl-[1,2,4]triazol-1-yl)-1,1-dimethyl-propylamino]-1-hydroxy-ethyl)-}6-hydroxy-4H-benzo[1,4]oxazin-3-one;
- 7-{2-[3-(3-benzo[1,3]dioxol-5-yl-5-methyl-[1,2,4]triazol-1-yl)-1,1-dimethyl-propylamino]-1-hydroxy-ethyl}-5-hydroxy-3H-benzoxazol-2-one and
- 8-{2-[3-(3-benzo[1,3]dioxol-5-yl-5-methyl-[1,2,4]triazol-1-yl)-1,1-dimethyl-propylamino]-1-hydroxy-ethyl}-6-hydroxy-2,2-dimethyl-4H-benzo[1,4]oxazin-3-one, optionally in the form of the pharmacologically acceptable acid addition salts thereof, as well as optionally in the form of the solvates and/or hydrates thereof.

In another aspect the present invention relates to the above-mentioned new compounds of formula 1 as pharmaceutical compositions. The present invention also relates to the use of the above-mentioned compounds of formula 1 for preparing a pharmaceutical composition for the treatment of respiratory complaints.

The present invention preferably relates to the use of the above-mentioned compounds of formula 1 for preparing a pharmaceutical composition for the treatment of respiratory complaints selected from the group comprising obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome) and all forms of pulmonary edema.

Preferably the compounds of formula 1 are used to prepare a pharmaceutical composition for the treatment of obstructive pulmonary diseases selected from among COPD (chronic obstructive pulmonary disease), bronchial asthma, paediatric asthma, severe asthma, acute asthma attacks and chronic bronchitis, while it is particularly preferable according to the invention to use them for preparing a pharmaceutical composition for the treatment of bronchial asthma.

Preferably also, the compounds of formula 1 are used to prepare a pharmaceutical composition for the treatment of pulmonary emphysema which has its origins in COPD (chronic obstructive pulmonary disease) or α1-proteinase inhibitor deficiency.

Preferably also, the compounds of formula 1 are used to prepare a pharmaceutical composition for the treatment of restrictive pulmonary diseases selected from among allergic alveolitis, restrictive pulmonary diseases triggered by work-related noxious substances, such as asbestosis or silicosis, and restriction caused by lung tumours, such as for example lymphangiosis carcinomatosa, bronchoalveolar carcinoma and lymphomas.

Preferably also, the compounds of formula 1 are used to prepare a pharmaceutical composition for the treatment of interstitial pulmonary diseases selected from among pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematodes, systemic sclerodermy or sarcoidosis, granulomatoses, such as for example Boeck's disease, idiopathic interstitial pneumonia or idiopathic pulmonary fibrosis (IPF).

Preferably also, the compounds of formula 1 are used to prepare a pharmaceutical composition for the treatment of cystic fibrosis or mucoviscidosis.

Preferably also, the compounds of formula 1 are used to prepare a pharmaceutical composition for the treatment of bronchitis, such as for example bronchitis caused by bacterial or viral infection, allergic bronchitis and toxic bronchitis.

Preferably also, the compounds of formula 1 are used to prepare a pharmaceutical composition for the treatment of bronchiectasis.

Preferably also, the compounds of formula 1 are used to prepare a pharmaceutical composition for the treatment of ARDS (adult respiratory distress syndrome).

Preferably also, the compounds of formula 1 are used to prepare a pharmaceutical composition for the treatment of pulmonary edema, for example toxic pulmonary edema after aspiration or inhalation of toxic substances and foreign substances.

Particularly preferably, the present invention relates to the use of the compounds of formula 1 for preparing a pharmaceutical composition for the treatment of asthma or COPD. Also of particular importance is the above-mentioned use of compounds of formula 1 for preparing a pharmaceutical composition for once-a-day treatment of inflammatory and obstructive respiratory complaints, particularly for the once-a-day treatment of asthma or COPD.

The present invention also relates to a process for the treatment of the above-mentioned diseases, characterised in that one or more of the above-mentioned compounds of general formula 1 are administered in therapeutically effective amounts. The present invention further relates to processes for the treatment of asthma or COPD, characterised in that one or more of the above-mentioned compounds of general formula 1 are administered once a day in therapeutically effective amounts.

In another aspect the present invention relates to the above-mentioned compounds of formula 1 in the form of the acid addition salts thereof with pharmacologically acceptable acids as well as optionally in the form of the solvates and/or hydrates thereof.

By acid addition salts with pharmacologically acceptable acids are meant for example salts selected from the group comprising the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

By the term "$C_{1-6}$-alkyl" (including those which are part of other groups) are meant branched and unbranched alkyl groups with 1 to 6 carbon atoms, and by the term "$C_{1-4}$-alkyl" are meant branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1, 2- and 3-butynyl, 1-methyl-1-propynyl, 1-methyl-2-propynyl etc.

By the term "$C_{5-6}$-cycloalkyl" (including those which are part of other groups) are meant cyclic alkyl groups with 5 or 6 carbon atoms. Examples include: cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Preferred halogen atoms are fluorine, chlorine, particularly preferably fluorine. Examples include: $CF_3$, $CHF_2$, $CH_2F$, $CH_2CF_3$.

Halogen within the scope of the present invention denotes fluorine, chlorine, bromine or iodine. Unless stated to the contrary, fluorine, chlorine and bromine are regarded as preferred halogens.

Compounds of general formula 1 may have acid groups, predominantly carboxyl groups, and/or basic groups such as e.g. amino functions. Compounds of general formula 1 may therefore be in the form of internal salts, salts with pharmaceutically acceptable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically acceptable bases such as alkali or alkaline earth metal hydroxides or carbonates, zinc or ammonium hydroxides or organic amines such as e.g. diethylamine, triethylamine, triethanolamine etc.

As stated previously, the compounds of formula 1 may be converted into the salts thereof, particularly, for pharmaceutical use, into the physiologically and pharmacologically acceptable salts thereof. These salts may be present on the one hand as physiologically and pharmacologically acceptable acid addition salts of the compounds of formula 1 with inorganic or organic acids. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. Mixtures of these acids may also be used. In order to prepare the alkali and alkaline earth metal salts of the compound of formula 1 it is preferable to use the alkali and alkaline earth metal hydroxides and hydrides, while the hydroxides and hydrides of the alkali metals, particularly sodium and potassium, are preferred, sodium and potassium hydroxide being particularly preferred.

If desired, the compounds of general formula 1 may be converted into the salts thereof, particularly, for pharmaceutical use, into the pharmacologically acceptable salts thereof with an inorganic or organic acid. Suitable acids for this purpose include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. Mixtures of these acids may also be used.

The invention relates to the compounds in question, optionally in the form of the individual optical isomers, mixtures of the individual enantiomers or racemates, in the form of the tautomers and in the form of the free bases or corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

The compounds according to the invention may be in the form of racemates, but may also be obtained as pure enantiomers, i.e. in the (R) or (S) form. Compounds in the form of racemates or in the (R) form are preferred.

The compounds according to the invention may be prepared analogously to methods already known in the art. Suitable methods of production are known for example from U.S. Pat. Nos. 4,460,581 and 4,154,829, the whole of which is hereby incorporated by reference.

The following Examples serve to further illustrate and clarify the present invention without restricting its subject matter to the Examples provided by way of illustration.

Synthesis of the Intermediate Products 1-9

Intermediate Product 1: 1,1-dimethyl-3-(5-methyl-3-p-tolyl-[1,2,4]triazol-1-yl)-propylamine

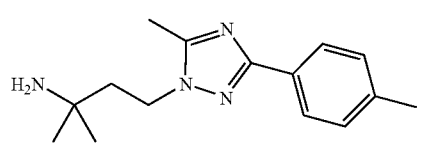

a) 4-methyl-benzoic acid-(1-imino-ethyl)-hydrazide 1.65 g (72 mmol) sodium are dissolved in 80 mL ethanol. 8.89 g (72 mmol) ethyl acetimidate hydrochloride in 160 mL ethanol are added at ambient temperature and the precipitated sodium chloride is filtered off. The filtrate is combined with 6.00 g (40 mmol) 4-methyl-benzoic acid hydrazide and stirred overnight. The reaction mixture is evaporated down and cooled. The precipitated solid is filtered off and washed with cold ethanol and diethyl ether (5.7 g white solid). A further 1.2 g solid are obtained from the filtrate after distillation of the solvents and recrystallisation from ethanol.

Yield: 6.93 g (91%); mass spectroscopy $[M+H]^+=192$.

b) 5-methyl-3-p-tolyl-r1,2,4]triazole 7.58 g (40 mmol) 4-methyl-benzoic acid-(1-imino-ethyl)-hydrazide are heated to 180° C. with stirring for 30 minutes. After cooling the solid is dissolved in chloroform. The precipitate formed on cooling is suction filtered and recrystallised from chloroform.

Yield: 4.82 g (70%); mass spectroscopy $[M+H]^+=174$.

c) tert-butyl [1,1-dimethyl-3-(5-methyl-3-p-tolyl-[1,2,4]triazol-1-yl)-propyl]-carbamate 1.35 g (34 mmol, 60%) sodium hydride are added at 0° C. to a solution of 4.87 g (28 mmol) 5-methyl-3-p-tolyl-[1,2,4]triazole in 40 mL of DMPU. The reaction mixture is heated to ambient temperature and then stirred for one hour. 9.35 g (42 mmol) tert-butyl (3-chloro-1,1-dimethyl-propyl)-carbamate and 1.87 g (5 mmol) tetrabutylammonium iodide are added and the mixture is stirred overnight at ambient temperature and then for 2 hours at 80° C. The mixture is combined with water and ethyl acetate, the aqueous phase is separated off and extracted with ethyl acetate. The combined organic phases are washed with water and sodium chloride solution, dried with sodium sulphate and evaporated down. The residue is purified by column chromatography (silica gel; petroleum ether/ethyl acetate=1:1). Oil. Yield: 2.97 g (30%); mass spectroscopy $[M+H]^+=359$.

d) 1,1-dimethyl-3-(5-methyl-3-p-tolyl-[1,2,4]triazol-1-yl)-propylamine

A total of 11 mL trifluoroacetic acid are added dropwise to a solution of 2.97 g (8.3 mmol) tert-butyl [1,1-dimethyl-3-(5-methyl-3-p-tolyl-[1,2,4]triazol-1-yl)-propyl]-carbamate in 80 mL dichloromethane and the mixture is stirred overnight at ambient temperature. The solvent is distilled off and the residue is combined with diethyl ether and stirred. The precipitated solid is filtered off and washed.

Yield: 2.11 g (68%, trifluoroacetate); mass spectroscopy $[M+H]^+=259$.

Intermediate Product 2: 3-[3-(4-fluoro-phenyl)-5-methyl-1,2,4]triazol-1-yl]-1,1-dimethyl-propylamine

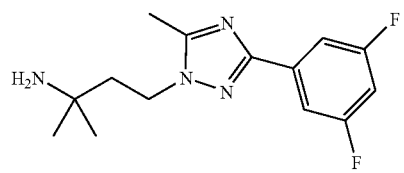

a) 4-fluoro-benzoic acid-(1-imino-ethyl)-hydrazide

Prepared from 7.2 g (58 mmol) ethyl acetimidate hydrochloride and 5.00 g (32 mmol) 4-fluoro-benzoic acid hydrazide analogously to the method described for intermediate product 1a). Yield: 5.78 g (91%); mass spectroscopy $[M+H]^+=196$.

b) 3-(4-fluoro-phenyl)-5-methyl-[1,2,4]triazole

The preparation is carried out analogously to the procedure laid down for intermediate product 1b) from 5.77 g (30 mmol) 4-fluoro-benzoic acid-(1-imino-ethyl)-hydrazide.

Yield: 4.11 g (78%); mass spectroscopy $[M+H]^+=178$.

c) tert-butyl {3-[3-(4-fluoro-phenyl)-5-methyl-[1,2,4]triazol-1-yl]-1,1-dimethyl-propyl}-carbamate 5.88 g (33 mmol) 3-(4-fluoro-phenyl)-5-methyl-[1,2,4]triazole are dissolved in 40 mL DMPU and reacted as described for intermediate product 1c) with 11.04 g (50 mmol) of tert-butyl (3-chloro-1,1-dimethyl-propyl)-carbamate, 1.59 g (40 mmol, 60%) sodium hydride and 2.21 g (6 mmol) tetrabutylammonium iodide.

Yield: 4.22 g (35%); mass spectroscopy $[M+H]^+=363$.

d) 3-[3-(4-fluoro-phenyl)-5-methyl-[1,2,4]triazol-1-yl]-1,1-dimethyl-propylamine Obtained from the reaction of 4.22 g (11.6 mmol) tert-butyl{3-[3-(4-fluoro-phenyl)-5-methyl-[1,2,4]triazol-1-yl]-1,1-dimethyl-propyl}-carbamate in 100 mL dichloromethane and 15 mL trifluoroacetic acid. White solid.

Yield: 4.43 g (trifluoroacetate); mass spectroscopy $[M+H]^+=263$.

Intermediate Product 3: 3-[3-(3,5-difluoro-phenyl)-5-methyl-[1,2,4triazol-1-yl]-1,1-dimethyl-propylamine

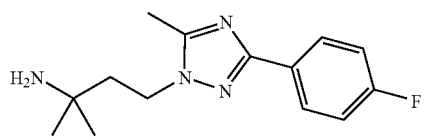

a) 3,5-difluoro-benzoic acid-(1-imino-ethyl)-hydrazide

Obtained from 4.91 g (40 mmol) ethyl acetimidate hydrochloride and 3.80 g (22 mmol) 3.5 difluoro-benzoic acid hydrazide analogously to the procedure laid down for intermediate product 1a). Yield: 4.49 g (95%); mass spectroscopy $[M+H]^+=214$.

b) 3-(3,5-difluoro-phenyl)-5-methyl-1,2,4]triazole

Prepared from 4.61 g (22 mmol) 3,5-difluoro-benzoic acid-(1-imino-ethyl)-hydrazide.

Yield: 3.81 g (91%); mass spectroscopy $[M+H]^+=196$.

c) tert-butyl {3-[3-(3,5-difluoro-phenyl)-5-methyl-[1,2,4]triazol-1-yl]-1,1-dimethyl-propyl}-carbamate 3.74 g (19 mmol) 3-(3,5-difluoro-phenyl)-5-methyl-[1,2,4]triazole in 25 mL DMPU are reacted with 0.92 g (23 mmol, 60%) sodium hydride, 6.37 g (29 mmol) tert-butyl (3-chloro-1,1-dimethyl-propyl)-carbamate and 1.27 g (3.5 mmol) tetrabutylammonium iodide analogously to intermediate product 1c). Oil.

Yield: 2.62 g (36%); mass spectroscopy $[M+H]^+=381$.

d) 3-[3-(3,5-difluoro-phenyl)-5-methyl-[1,2,4]triazol-1-yl]-1,1-dimethyl-propylamine 2.62 g (6.9 mmol) tert-butyl {3-[3-(3,5-difluoro-phenyl)-5-methyl-[1,2,4]triazol-1-yl]-1,1-dimethyl-propyl}-carbamate in 65 mL dichloromethane are reacted with 9 mL trifluoroacetic acid as described for intermediate product 1d). White solid.

Yield: 2.11 g (trifluoroacetate); mass spectroscopy $[M+H]^+=281$.

Intermediate Product 4: 3-[5-ethyl-3-(4-methoxy-phenyl)-[1,2,4]triazol-1-yl]-1,1-dimethyl-propylamine

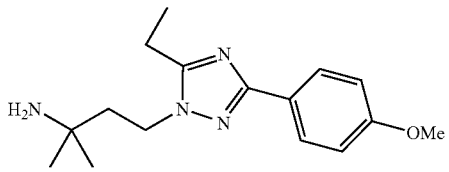

a) 4-methoxy-benzoic acid-(1-imino-propyl)-hydrazide

Prepared from 4.90 g (45 mmol) propioamidine hydrochloride and 5.00 g (30 mmol) 4-methoxy-benzoic acid hydrazide analogously to the procedure laid down for intermediate product 1a). After distillation of the ethanol 10.0 g crude product are obtained, which are reacted without any further purification.

b) 5-ethyl-3-(4-methoxy-phenyl)-[1,2,4]triazole 9.99 g (60%, approx. 28 mmol) of 4-methoxy-benzoic acid-(1-imino-propyl)-hydrazide are heated to 150° C. for two hours. After cooling the melt is purified by chromatography on a silica gel column (petroleum ether/ethyl acetate=3:7). Light yellow solid.

Yield: 4.56 g (75% over two steps); mass spectroscopy [M+H]$^+$=204.

c) tert-butyl {3-[5-ethyl-3-(4-methoxy-phenyl)-[1,2,4]triazol-1-yl]-1,1-dimethyl-propyyl-carbamate 4.30 g (21.2 mmol) 5-ethyl-3-(4-methoxy-phenyl)-[1,2,4]triazole are dissolved in 30 mL DMPU and cooled to 0° C. Under a protective gas atmosphere 1.02 g (24 mmol, 60%) sodium hydride are then added batchwise and the reaction mixture is slowly heated to ambient temperature and then stirred for one hour. 6.10 g (27.5 mmol) tert-butyl (3-chloro-1,1-dimethyl-propyl)-carbamate and 1.41 g (3.8 mmol) tetrabutylammonium iodide are added. The mixture is stirred overnight and then the reaction is ended by the addition of water and ethyl acetate. The aqueous phase is separated off and extracted with ethyl acetate. The combined organic phases are washed with sodium chloride solution, dried with sodium sulphate and evaporated down. The oil remaining is purified by chromatography on a silica gel column (petroleum ether/ethyl acetate=3:7).

Yield: 6.82 g (83%); mass spectroscopy [M+H]$^+$=389.

d) 3-[5-ethyl-3-(4-methoxy-phenyl)-[1,2,4]triazol-1-yl]-1,1-dimethyl-propylamine A total of 20 mL trifluoroacetic acid are added dropwise to a solution of 6.81 g (17.5 mmol) tert-butyl {3-[5-ethyl-3-(4-methoxy-phenyl)-[1,2,4]triazol-1-yl]-1,1-dimethyl-propyl-carbamate in 150 mL dichloromethane. After three hours stirring at ambient temperature the solution is evaporated down and the oil remaining is combined with diethyl ether. The white solid precipitated is filtered off, washed with diethyl ether and dried. Yield: 7.86 g (trifluoroacetate); mass spectroscopy [M+H]$^+$=289.

Intermediate product 5: methyl 3-[1-(3-amino-3-methyl-butyl)-5-methyl-1H-[1,2,4]triazol-3-yl]-benzoate

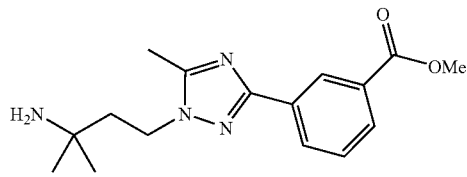

a) methyl 3-[N'-benzyloxycarbonyl-hydrazinocarbonyl)-benzoate 10.80 g (54.4 mmol) methyl 3-chlorocarbonyl-benzoate in 100 mL diethyl ether are added dropwise to a solution of 9.04 g (54.4 mmol) benzyl hydrazine carboxylate in 100 mL diethyl ether, 100 mL dichloromethane and 4.83 mL pyridine while cooling with an ice bath. The reaction mixture is stirred overnight at ambient temperature and then combined with water. The precipitated solid is filtered off and washed with diethyl ether. White solid.

Yield: 14.1 g (79%); mass spectroscopy [M–H]$^+$=327.

b) methyl 3-hydrazinocarbonyl-benzoate 14.6 g (44.5 mmol) methyl 3-[N'-benzyloxycarbonyl-hydrazinocarbonyl)-benzoate are dissolved in 75 mL methanol and hydrogenated in the presence of palladium on charcoal (10%) at ambient temperature and 3 bar hydrogen pressure. The catalyst is filtered off and the filtrate is freed from solvent. White solid.

Yield: 7.98 g (92%); mass spectroscopy [M+H]$^+$=195.

c) methyl 3-[N'-(1-imino-ethyl)-hydrazinocarbonyl]-benzoate

Prepared analogously to the method described for intermediate product 1a) from methyl 3-hydrazinocarbonyl-benzoate and ethyl acetimidate hydrochloride. White solid.

Yield: 8.60 g (90%); mass spectroscopy [M+H]$^+$=236.

d) methyl 3-(5-methyl-1H-[1,2,4]triazol-3-yl)-benzoate 8.10 g (34.4 mmol) methyl 3-[N'-(1-imino-ethyl)-hydrazinocarbonyl]-benzoate are heated to 180° C. for 30 minutes. 80 mL chloroform are added to the solid obtained after cooling. The suspension is filtered and the product is dried. White solid.

Yield: 4.03 g (55%); mass spectroscopy [M+H]$^+$=218.

e) methyl 3-[1-(3-tert-butoxycarbonylamino-3-methyl-butyl)-5-methyl-1H-[1,2,4]triazol-3-yl-benzoate 6.00 g (27.6 mmol) methyl 3-(5-methyl-1H-[1.24]triazol-3-yl)-benzoate and 9.19 g (41.4 mmol) tert-butyl (3-chloro-1,1-dimethyl-propyl)-carbamate are reacted as described for intermediate product 1c) and worked up. Yellow oil.

Yield: 5.96 g (54%); mass spectroscopy [M+H]$^+$=403.

f) methyl 3-[1-(3-amino-3-methyl-butyl)-5-methyl-1H-[1,2,4]triazol-3-yl]-benzoate Obtained from methyl 3-[1-(3-tert-butoxycarbonylamino-3-methyl-butyl)-5-methyl-1H-[1,2,4]triazol-3-yl-benzoate analogously to the method described for intermediate product 1d). Yield: 5.36 g (68%, ditrifluoroacetate); mass spectroscopy [M+H]$^+$=303.

Intermediate Product 6: methyl 3-[1-(3-amino-3-methyl-butyl)-5-methyl-1H-1,2,4triazol-3-yl]-benzoate

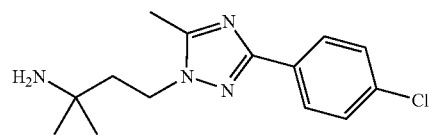

a) 4-chloro-benzoic acid N'-(1-imino-ethyl)-hydrazide 1.09 g (20 mmol) sodium methoxide in 20 mL ethanol are added to a solution of 1.91 g (20 mmol) acetamidine hydrochloride in 30 mL ethanol. The mixture is stirred for 30 minutes at ambient temperature and then filtered. The filtrate is combined with 2.3 g (13.5 mmol) 4-chlorobenzoic acid hydrazide, stirred overnight at ambient temperature, cooled with an ice bath and then filtered. The precipitate is washed with cold ethanol and dried. Yellow solid. Yield: 1.45 g (51%); mass spectroscopy [M+H]$^+$=212/214.

b) 3-(4-chloro-phenyl)-5-methyl-1H-[1,2,4]triazole 6.10 g (28.8 mmol) 4-chloro-benzoic acid N'-(1-imino-ethyl)-hydrazide are heated to 180° C. for 30 minutes. After cooling 2.3 g product are obtained from the residue by recrystallisation in chloroform. Evaporation of the mother liquor and subsequent purification of the residue by chromatography (silica gel, petroleum ether/ethyl acetate=1:6) yield an additional 1.22 g of product. White solid.

Yield: 3.51 g (63%); mass spectroscopy [M+H]$^+$=194/196.

c) tert-butyl {3-[3-(4-chloro-phenyl)-5-methyl-[1,2,4]triazol-1-yl]-1,1-dimethyl-propyl}-carbamate 3.48 g (18.0 mmol) 3-(4-chloro-phenyl)-5-methyl-1H-[1.24]triazole and 5.98 g (27.0 mmol) tert-butyl (3-chloro-1,1-dimethyl-propyl)-carbamate are reacted as described for intermediate product 1c) and worked up. Yellow oil.

Yield: 3.89 g (57%); mass spectroscopy [M+H]$^+$=379/381.

d) methyl 3-[1-(3-amino-3-methyl-butyl)-5-methyl-1H-[1,2,4]triazol-3-yl]-benzoate Obtained from tert-butyl {3-[3-(4-chloro-phenyl)-5-methyl-[1,2,4]triazol-1-yl]-1,1-dimethyl-propyl}-carbamate as described for intermediate product 1d).

Yield: 3.65 g (trifluoroacetate); mass spectroscopy [M+H]$^+$=279/281.

Intermediate Product 7: 1,1-dimethyl-3-[5-methyl-3-(4-trifluoromethyl-phenyl)-[1,2,4]triazol-1-yl]-propylamine

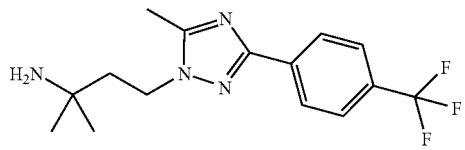

a) 4-trifluoromethyl-benzoic acid N'-(1-imino-ethyl)-hydrazide 4.78 g (23.4 mmol) 4-(trifluoromethyl)benzoic acid hydrazide and 5.21 g (42.1 mmol) ethyl acetimidate hydrochloride are reacted as described for intermediate product 1a).

Yield: 6.02 g; mass spectroscopy [M+H]$^+$=246.

b) 5-methyl-3-(4-trifluoromethyl-phenyl)-1H-[1,2,4]triazole

Prepared from 6.02 g (24.6 mmol) 4-trifluoromethyl-benzoic acid N'-(1-imino-ethyl)-hydrazide analogously to the method described for intermediate product 1b). White solid.

Yield: 4.76 g (85%); mass spectroscopy [M+H]$^+$=228.

c) tert-butyl {1,1-dimethyl-3-[5-methyl-3-(4-trifluoromethyl-phenyl)-[1,2,4]triazol-1-yl]-propyl}-carbamate The target compound is obtained analogously to the method described for intermediate product 1c) from 4.90 g (21.6 mmol) 5-methyl-3-(4-trifluoromethyl-phenyl)-1H-[1,2,4]triazol and 7.17 g (32.4 mmol) tert-butyl (3-chloro-1,1-dimethyl-propyl)-carbamate. White solid. Yield: 5.06 g (57%); mass spectroscopy [M+H]$^+$=413.

d) 1,1-dimethyl-3-[5-methyl-3-(4-trifluoromethyl-phenyl)-[1,2,4]triazol-1-yl]-propylamine Prepared according to the method described for intermediate product 1d) from tert-butyl {1,1-dimethyl-3-[5-methyl-3-(4-trifluoromethyl-phenyl)-[1,2,4]triazol-1-yl]-propyl}-carbamate. White solid. Yield: 4.72 g (trifluoroacetate); mass spectroscopy [M+H]$^+$=313.

Intermediate Product 8: 3-(3-benzo[1,3dioxol-5-yl-5-methyl-[1,2,4]triazol-1-yl)-1,1-dimethyl-propylamine

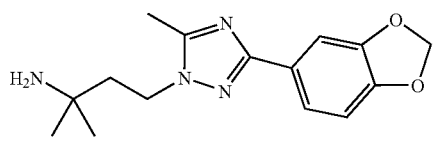

The preparation is carried out analogously to the syntheses described hereinbefore. Mass spectroscopy [M+H]$^+$=289.

Intermediate Product 9: 3-[3-(4-methoxy-phenyl)-5-methyl-[1,2,4]triazol-1-yl]-1,1-dimethyl-propylamine

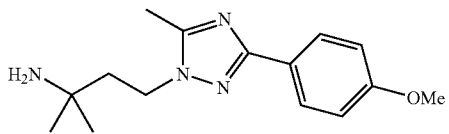

a) 4-methoxy-benzoic acid N'-(1-imino-ethyl)-hydrazide 4.6 g (0.20 mol) sodium in 200 mL ethanol are combined at ambient temperature with a solution of 25 g (0.20 mol) ethyl acetimidate hydrochloride in 200 mL ethanol. The sodium chloride precipitated is suction filtered and 33.2 g (0.20 mol) 4-methoxybenzoic acid hydrazide are added to the filtrate. The reaction mixture is stirred overnight at ambient temperature and then cooled. The precipitate formed is separated off and washed with ethanol and diethyl ether. Yield: 33.6 g (81%); melting range=179-181° C.

b) 3-(4-methoxy-phenyl)-5-methyl-1H-[1,2,4]triazole 33.6 g (162 mmol) 4-methoxy-benzoic acid N'-(1-imino-ethyl)-hydrazide are heated to 180° C. for 30 minutes. After cooling the solidified melt is dissolved in 250 mL chloroform and repeatedly extracted with aqueous sodium hydroxide solution. The aqueous phases are combined, washed with chloroform, filtered and adjusted to an acid pH by the addition of glacial acetic acid. The precipitated solid is suction filtered, washed with water and dissolved by heating in chloroform. The solvent is evaporated down and the residue is filtered. The solid is washed with chloroform and diethyl ether.

Yield: 23.1 g (75%); melting range=169-171° C.

c) 3-[3-(4-methoxy-phenyl)-5-methyl-[1,2,4triazol-1-yl]-1,1-dimethyl-propylamine The target compound is obtained from the reaction of 21.4 g (113 mmol) 3-(4-methoxy-phenyl)-5-methyl-1H-[1,2,4]triazole and 25 g (119 mmol) (3-chloro-1,1-dimethyl-propyl)-[1-phenyl-methylidene]-amine. The product is dissolved in 100 mL acetone and acidified with 8.5 mL 32% aqueous hydrochloric acid and cooled. The hydrochloride precipitated is suction filtered and washed with acetone and diethyl ether.

Yield: 20.3 g; melting range=190-194° C.

General Method 1:

1 mmol of 6-benzyloxy-8-(2-ethoxy-2-hydroxy-acetyl)-4H-benzo[1,4]oxazin-3-one and 1 mmol amine are stirred for 15 minutes in 5 mL tetrahydrofuran at 60° C. The mixture is cooled to 0° C. and under an argon atmosphere 1.5 mL of a 2 molar solution of lithium borohydride in tetrahydrofuran is added dropwise. The mixture is stirred for 15 min at 0° C., combined with 10 mL dichloromethane and 3 mL water, stirred for a further hour at ambient temperature and then filtered through kieselguhr, eluting with dichloromethane. The eluate is freed from the solvent and the residue is, if necessary, purified by chromatography. The benzylether thus obtained is dissolved in methanol and hydrogenated at 2.5 bar and ambient temperature with palladium on charcoal (10%) as catalyst. Then the catalyst is separated off and the crude product is purified by chromatography (reverse phase, acetonitrile/water gradient with 0.1% trifluoroacetic acid).

General Method 2:

1 mmol of 6-benzyloxy-8-(2-ethoxy-2-hydroxy-acetyl)-4H-benzo[1,4]oxazin-3-one and 1 mmol amine are suspended in 5 mL ethanol and heated to 70° C. The resulting solution is stirred for one hour at 70° C. and then cooled to ambient temperature. After the addition of 113 mg (3 mmol) sodium borohydride the mixture is stirred for 3 hours at ambient temperature, combined with 0.7 mL saturated potassium carbonate solution and stirred for a further 30 minutes. The mixture is filtered through aluminium oxide (basic), washed repeatedly with dichloromethane/methanol=15:1, evaporated down and chromatographed (silica gel; dichloromethane with 0-10% methanol:ammonia=9:1). The benzylether thus obtained is dissolved in 10 mL methanol and hydrogenated at 1 bar hydrogen pressure with palladium on charcoal as catalyst. Then the catalyst is filtered off and the filtrate is evaporated down.

EXAMPLE 1

8-(2-{3-[3-(4-fluoro-phenyl)-5-methyl-[1,2,4]triazol-1-yl]-1,1-dimethyl-propylamino}-1-hydroxy-ethyl)-6-hydroxy-4H-benzo[1,4]oxazin-3-one

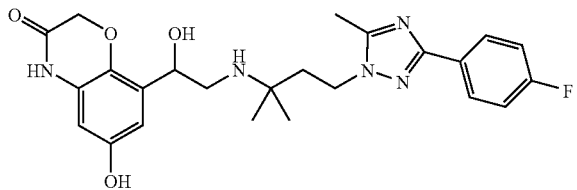

Obtained from the reaction of 6-benzyloxy-8-(2-ethoxy-2-hydroxy-acetyl)-4H-benzo[1,4]oxazin-3-one and 3-[3-(4-fluoro-phenyl)-5-methyl-[1,2,4]triazol-1-yl]-1,1-dimethyl-propylamine according to General Method 1. The final purification is carried out by chromatography (reverse phase, acetonitrile/water gradient with 0.1% trifluoroacetic acid). White solid.

Yield: 134 mg (29%, trifluoroacetate); mass spectroscopy $[M+H]^+=470$.

EXAMPLE 2

8-{2-[1,1-dimethyl-3-(5-methyl-3-p-tolyl-[1,2,4]triazol-1yl)-propylamino]-1-hydroxy-ethyl}-6-hydroxy-4H-benzo[1,4]oxazin-3one

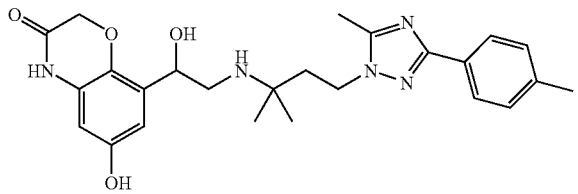

Prepared from 6-benzyloxy-8-(2-ethoxy-2-hydroxy-acetyl)-4H-benzo[1,4]oxazin-3-one and 1,1-dimethyl-3-(5-methyl-3-p-tolyl-[1,2,4]triazol-1-yl)-propylamine according to General Method 1. Light beige solid.

Yield: 283 mg (49%, trifluoroacetate); mass spectroscopy $[M+H]^+=466$.

EXAMPLE 3

8-(2-{1,1-dimethyl-3-[5-methyl-3-(4-trifluoromethyl-phenyl)-[1,2,4]triazol-1-yl]-propylamino}-1-hydroxy-ethyl)-6-hydroxy-4H-benzo[1,4]oxazin-3-one

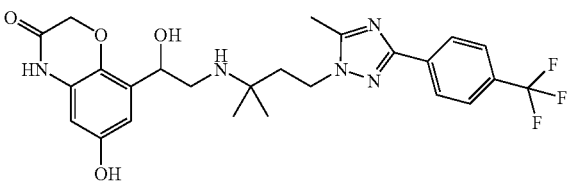

Prepared from 6-benzyloxy-8-(2-ethoxy-2-hydroxy-acetyl)-4H-benzo[1,4]oxazin-3-one and 1,1-dimethyl-3-[5-methyl-3-(4-trifluoromethyl-phenyl)-[1,2,4]triazol-1-yl]-propylamine analogously to General Method 1. Beige solid.

Yield: 234 mg (37%, trifluoroacetate); mass spectroscopy $[M+H]^+=520$.

EXAMPLE 4

8-(2-{3-[3-(3,5-difluoro-phenyl)-5-methyl-[1,2,4]triazol-1-yl]-1,1-dimethyl-propylamino}-1-hydroxy-ethyl)-6-hydroxy-4H-benzo[1,4]oxazin-3-one

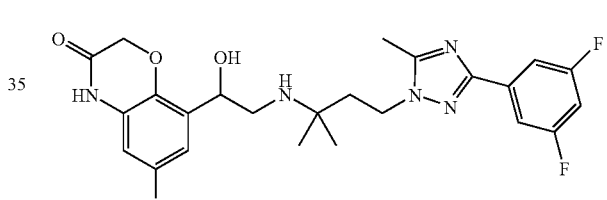

Prepared from 6-benzyloxy-8-(2-ethoxy-2-hydroxy-acetyl)-4H-benzo[1,4]oxazin-3-one and 3-[3-(3,5-difluoro-phenyl)-5-methyl-[1,2,4]triazol-1-yl]-1,1-dimethyl-propylamine according to General Method 1. White solid.

Yield: 208 mg (35%, trifluoroacetate); mass spectroscopy $[M+H]^+=488$.

EXAMPLE 5

3-(1-{3-[2-hydroxy-2-(6-hydroxy-3-oxo-3,4-dihydro-2H-benzo[1,4]oxazin-8-yl)-ethylamino]-3-methyl-butyl}-5-methyl-1H-[1,2,4]triazol-3-yl-benzoic acid

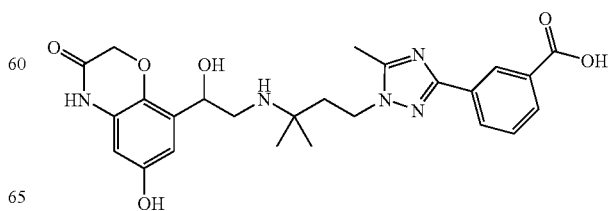

a) methyl 3-(1-{3-[2-(6-benzyloxy-3-oxo-3,4-dihydro-2H-benzo[14,]oxazin-8-yl)-2-hydroxy-ethylamino]-3-methyl-butyl}-5-methyl-1H-[1,2,4]triazol-3-yl)-benzoate Prepared from 6-benzyloxy-8-(2-ethoxy-2-hydroxy-acetyl)-4H-benzo[1,4]oxazin-3-one and methyl 3-[1-(3-amino-3-methyl-butyl)-5-methyl-1H-[1,2,4]triazol-3-yl]-benzoate analogously to General Method 1. The final purification is carried out by chromatography (reverse phase, acetonitrile/water gradient with 0.1% trifluoroacetic acid).

Yield: 550 mg (77%, trifluoroacetate); mass spectroscopy [M+H]⁺=510.

b) 3(1-{3-[2-(6-benzyloxy-3-oxo-3,4-dihydro-2H-benzo[1,4]oxazin-8-yl)-2 hydroxy-ethylamino]-3-methyl-butyl{-5-methyl-1H-[1,2,4]triazol-3-yl)-benzoic acid A solution of 550 mg (0.72 mmol) methyl 3-(1-{3-[2-(6-benzyloxy-3-oxo-3,4-dihydro -2H-benzol[1,4]oxazin-8-yl)-2-hydroxy-ethylamino]-3-methyl-butyl}-5-methyl-1H-[1,2,4]triazol-3-yl)-benzoate trifluoroacetate in 10 mL methanol is combined with 2 mL of a 2 molar sodium hydroxide solution and refluxed for 30 minutes. After the methanol has been distilled off 5 mL water, 10 mL n-butanol and 5 mL acetic acid are added. The precipitate formed is suction filtered and washed with diethyl ether. Brown solid.

Yield: 300 mg (56%, trifluoroacetate); mass spectroscopy [M+H]⁺=586.

c) 3-(1-{3-[2-hydroxy-2-(6-hydroxy-3-oxo-3,4-dihydro-2H-benzo[1,4]oxazin-8-yl)-ethylamino]-3-methyl-butyl}-5-methyl-1H-[1,2,4]triazol-3-yl-benzoic acid 250 mg (0.36 mmol) 3-(1-{3-[2-(6-benzyloxy-3-oxo-3,4-dihydro-2H-benzo[1,4]oxazin-8-yl)-2-hydroxy-ethylamino]-3-methyl-butyl}-5-methyl-1H-[1,2,4]triazol-3-yl)-benzoic acid trifluoroacetate are dissolved in 5 mL methanol and hydrogenated at ambient temperature and 2.5 bar hydrogen pressure in the presence of palladium on charcoal (10%). The catalyst is suction filtered, the filtrate is evaporated down and the residue is purified by chromatography (reverse phase, acetonitrile/water gradient with 0.1% trifluoroacetic acid). Yellow solid. Yield: 62 mg (28%, trifluoroacetate); mass spectroscopy [M+H]⁺=496.

EXAMPLE 6

8-(2-{3-[3-(4-chloro-phenyl)-5-methyl-[1,2,4]triazol-1-yl]-1,1-dimethyl -propylamino}-1-hydroxy-ethyl)-6-hydroxy-4H-benzol[1,4]oxazin-3-one

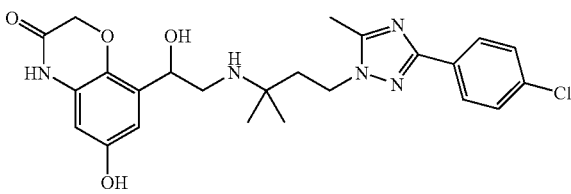

a) 6-benzyloxy-8-(2-{3-[3-(4-chloro-phenyl)-5-methyl-[1,2,4]triazol-1-yl]-1,1-dimethyl-propylamino}-1-hydroxy-ethyl)-4H-benzo[1,4]oxazin-3one Prepared from 6-benzyloxy-8-(2-ethoxy-2-hydroxy-acetyl)-4H-benzo[1,4]oxazin-3-one and 3-[3-(4-chloro-phenyl)-5-methyl-[1,2,4]triazol-1-yl]-1,1-dimethyl-propylamine analogously to General Method 1. The crude product is purified by chromatography (reverse phase, acetonitrile/water gradient with 0.1% trifluoroacetic acid).

Yield: 550 mg (80%, trifluoroacetate); mass spectroscopy [M+H]⁺=576.

8-(2-{3-[3-(4-chloro-phenyl)-5-methyl-[1,2,4]triazol-1-yl]-1,1-dimethyl -propylamino}-1-hydroxy-ethyl)-6-hydroxy-4H-benzol[1,4]oxazin-3-one 550 mg (0.80 mmol) 6-benzyloxy-8-(2-{3-[3-(4-chloro-phenyl)-5-methyl-[1,2,4]triazol-1-1-yl]-1,1-dimethyl-propylamino}-1-hydroxy-ethyl)-4H-benzo[1,4]oxazin-3-one are dissolved in 3 mL dichloromethane and cooled to −78° C. 2 mL of a 1 molar solution of boron tribromide in dichloromethane are added dropwise and the mixture is heated to ambient temperature. It is stirred for 10 minutes at this temperature and then combined with 10 mL dichloromethane and 3 mL water and stirred for 30 minutes. It is filtered through kieselguhr, eluting with dichloromethane and methanol. The eluate is evaporated down and the residue is purified by chromatography (reverse phase, acetonitrile/water gradient with 0.1% trifluoroacetic acid). White solid.

Yield: 29 mg (6%, trifluoroacetate); mass spectroscopy [M+H]⁺=486/8.

EXAMPLE 7

8-(2-{3-[5-ethyl-3-(4-methoxy-phenyl)-[1,2,4triazol-1-yl]-1,1-dimethyl -propylamino}-1-hydroxy-ethyl)-6-hydroxy-4H-benzo[1,4]oxazin-3-one

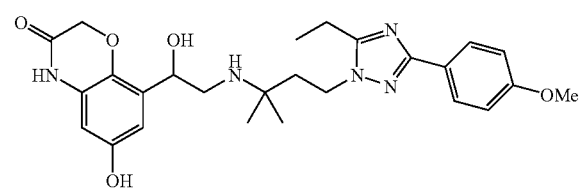

Prepared from 6-benzyloxy-8-(2-ethoxy-2-hydroxy-acetyl)-4H-benzo[1,4]oxazin-3-one and 3-[5-ethyl-3-(4-methoxy-phenyl)-[1,2,4]triazol-1-yl]-1,1-dimethyl-propylamine according to General Method 1.

Yield: 267 mg (44%, trifluoroacetate); mass spectroscopy [M+H]⁺=496.

EXAMPLE 8

6-hydroxy-8-(1-hydroxy-2-{3-[3-(4-methoxy-phenyl)-5-methyl-1,2,4]triazol-1yl]-1,1-dimethyl-propylamino}-ethyl)-4H-benzo[1,4]oxazin-3-one

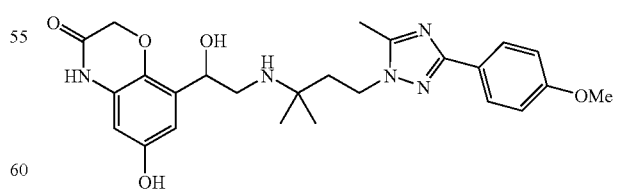

Prepared from 6-benzyloxy-8-(2-ethoxy-2-hydroxy-acetyl)-4H-benzo[1,4]oxazin-3-one and 3-[3-(4-methoxy-phenyl)-5-methyl-[1,2,4]triazol-1-yl]-1,1-dimethyl-propylamine according to General Method 2. Yield: 217 mg (45%); mass spectroscopy [M+H]⁺=482.

EXAMPLE 9

8-{2-[3-(3-benzo[1,3]dioxol-5-yl-5-methyl-[1,2,4]triazol-1-yl)-1,1-dimethyl-propylamino]-1-hydroxy-ethyl}-5-hydroxy-3H-benzoxazol-2-one

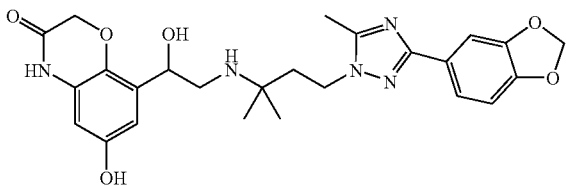

Prepared from 6-benzyloxy-8-(2-ethoxy-2-hydroxy-acetyl)-4H-benzo[1,4]oxazin-3-one and 3-(3-benzo[1,3]dioxol-5-yl-5-methyl-[1,2,4]triazol-1-yl)-1,1-dimethyl-propylamine according to General Method 2. Yield: 236 mg (48%); mass spectroscopy [M+H]$^+$=496.

EXAMPLE 10

7-{2-[3-(3-benzo[1,3]dioxol-5-yl-5-methyl-[1,2,4]triazol-1-yl)-1,1

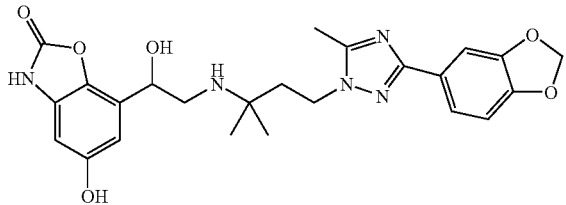

a) 7-acetyl-5-benzyloxy-3H-benzoxazol-2-one 52 g (0.53 mol) phosgene are piped into a solution of 121 g (0.47 mol) 1-(3-amino-5-benzyloxy-2-hydroxy-phenyl)-ethanone in 800 mL pyridine at 20 to 40° C. The reaction mixture is heated to 50° C. for 2 hours, then poured onto ice and acidified with conc. hydrochloric acid. A reddish-brown solid is isolated which is repeatedly recrystallised from ethanol with the addition of activated charcoal.

Yield: 67.5 g (51%); melting range: 163-166° C.

b) 5-benzyloxy-7-(2-ethoxy-2-hydroxy-acetyl)-3H-benzoxazol-2-one 20 g (71 mmol) 7-acetyl-5-benzyloxy-3H-benzoxazol-2-one and 8 g (72 mmol) selenium dioxide are refluxed for 8 hours in the presence of activated charcoal in 100 mL dioxane and 3.1 mL water, with stirring. The solid is filtered off, the solvent is distilled off and the residue is combined with 50 mL ethanol. The mixture is refluxed for 15 minutes and then filtered through activated charcoal. The solid precipitated on cooling is suction filtered after 3 hours and washed with ethanol and diethyl ether.

Yield: 7 g (29%); melting range: 140-143° C.

c) 17-{2-[3-(3-benzo[1,3]dioxol-5-yl-5-methyl-[1,2,4]triazol-1-yl) -1,1-dimethyl-propylamino]-1-hydroxy-ethyl}-5-hydroxy-3H-benzoxazol-2-one 72 mg (0.5 mmol) 5-benzyloxy-7-(2-ethoxy-2-hydroxy-acetyl)-3H-benzoxazol-2-one and 144 mg (0.5 mmol) 3-(3-benzo[1,3]dioxol-5-yl-5-methyl-[1,2,4]triazol-1-yl)-1,1-dimethyl-propylamine are stirred in 8 mL ethanol for 90 minutes at 80° C. After cooling to ambient temperature 19 mg (0.5 mmol) sodium borohydride are added and the mixture is stirred for 2 hours at ambient temperature. It is acidified with 1 N hydrochloric acid, stirred for 10 minutes and then made alkaline with potassium carbonate solution. The mixture is diluted with ethyl acetate and filtered through kieselguhr, during which time the aqueous constituents are separated off. The organic phase remaining is evaporated down and the residue is purified by chromatography. The benzylether thus obtained is dissolved in ethanol and hydrogenated with palladium on charcoal (10%) as catalyst at 2.5 bar and ambient temperature. Then the catalyst is separated off and the crude product is purified by chromatography (reverse phase, acetonitrile/water gradient with 0.1% trifluoroacetic acid).

Yield: 8 mg (3%, trifluoroacetate); mass spectroscopy [M+H]$^+$=482.

EXAMPLE 11

8-{2-[3-(3-benzo[1,3]dioxol-5-yl-5-methyl-[1,2,4]triazol-1-yl)-1,1-dimethyl-propylamino]-1-hydroxy-ethyl}-6-hydroxy-2,2-dimethyl-4H-benzo [1,4]oxazin-3-one

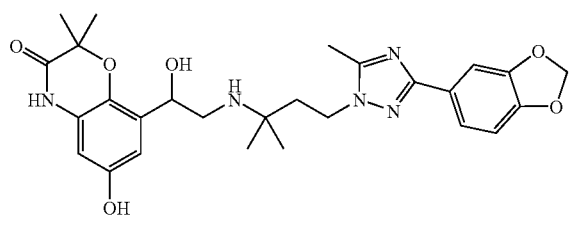

a) N-(3-acetyl-5-benzyloxy-2-hydroxy-phenyl)-2-bromo-2-methyl-propionamide 4.64 g (25 mmol) 2-bromo-2-methyl-propionyl chloride are added dropwise at 5-20° C. to a solution of 5.15 g (20 mmol) 1-(3-amino-5-benzyloxy-2-hydroxy-phenyl)-ethanone in 20 mL pyridine. After the addition has ended the mixture is stirred for 15 minutes, combined with ice water and 100 mL ethyl acetate and acidified with conc. hydrochloric acid. The organic phase is separated off, washed with water and dried with sodium sulphate. After the solvent has been distilled off the residue is crystallised from a diethyl ether/petroleum ether mixture.

Yield: 6.8 g (84%); melting range: 88-90° C.

b) 8-acetyl-6-benzyloxy-2,2-dimethyl-4H-benzo[1,4]oxazin-3-one 6.60 g (16.2 mmol) N-(3-acetyl-5-benzyloxy-2-hydroxy-phenyl)-2-bromo-2-methyl-propionamide and 2.76 g (20 mmol) potassium carbonate are stirred for 1 hour in 70 mL acetonitrile at reflux temperature. The solid is suction filtered, the filtrate is evaporated down and the residue is combined with 30 mL ethyl acetate. After further filtration and elimination of the solvent by distillation the crude product is crystallised from a little methanol.

Yield: 1.00 g (19%); mass spectroscopy [M+H]$^+$=326; melting range=148-150° C.

c) 6-benzyloxy-8-(2-ethoxy-2-hydroxy-acetyl)-2,2-dimethyl-4H-benzo[1,4]oxazin-3-one The preparation is carried out analogously to the method described for Example 10b) from 8-acetyl-6-benzyloxy-2,2-dimethyl-4H-benzo[1,4]oxazin-3-one.

d) 8-{2-[3-(3-benzo[1,3]dioxol-5-yl-5-methyl-[1,2,4]triazol-1-yl)-1,1-dimethyl-propylamino]-1-hydroxy-ethyl}-6-hydroxy-2,2-dimethyl-4H-benzo[1,4]oxazin-3-one Prepared from 385 mg (1 mmol) 6-benzyloxy-8-(2-ethoxy-2-hydroxy-acetyl)-2,2-dimethyl-4H-benzo[1,4]oxazin-3-one and 402 mg (1 mmol) 3-(3-benzo[1,3]dioxol-5-yl-5-methyl-[1,2,4]triazol-1-yl)-1,1-dimethyl-propylamine according to General Method 1.

Yield: 37 mg (6%, trifluoroacetate); mass spectroscopy $[M+H]^+=524$.

Suitable preparations for administering the compounds of formula 1 include for example tablets, capsules, suppositories, solutions, powders, etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc, and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations of active substances according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

In the preferred use of the compounds of formula 1 for the treatment of respiratory complaints according to the invention it is particularly preferred to use preparations or pharmaceutical formulations which are suitable for inhalation. Inhalable preparations include inhalable powders, propellant-containing metered-dose aerosols or propellant-free inhalable solutions. Within the scope of the present invention, the term propellant-free inhalable solutions also includes concentrates or sterile ready-to-use inhalable solutions. The formulations which may be used within the scope of the present invention are described in more detail in the next part of the specification.

The inhalable powders which may be used according to the invention may contain 1 either on its own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Within the scope of the inhalable powders according to the invention the excipients have a maximum average particle size of up to 250 µm, preferably between 10 and 150 µm, most preferably between 15 and 80 µm. In some cases it may seem appropriate to add finer excipient fractions with an average particle size of 1 to 9 µm to the excipients mentioned above. These finer excipients are also selected from the group of possible excipients listed hereinbefore. Finally, in order to prepare the inhalable powders according to the invention, micronised active substance 1, preferably with an average particle size of 0.5 to 10 µm, more preferably from 1 to 5 µm, is added to the excipient mixture. Processes for producing the inhalable powders according to the invention by grinding and micronising and lastly mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate.

In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the μg range. The compounds of formula 1 may also be used effectively above the μg range. The dosage may then be in the milligram range, for example.

In another aspect the present invention relates to the above-mentioned pharmaceutical formulations as such, which are characterised in that they contain a compound of formula 1, particularly preferably the above-mentioned pharmaceutical formulations administered by inhalation.

The following examples of formulations illustrate the present invention without restricting its scope:

| A) Ampoule solution | |
|---|---|
| active substance of formula 1 | 25 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| B) Metered-dose aerosol (suspension) | |
|---|---|
| active substance of formula 1 | 0.3 wt. % |
| sorbitolan trioleate | 0.6 wt. % |
| HFA134A:HFA227 2:1 | 99.1 wt. % |

The suspension is transferred into a conventional aerosol container with a metering valve. Preferably, 50 μl of suspension are delivered per spray. The active substance may also be metered in higher doses if desired.

| C) Metered-dose aerosol (solution) | |
| --- | --- |
| active substance of formula 1 | 0.3 wt. %. % |
| abs. ethanol | 20 wt. % |
| aqueous HCl 0.01 mol/l | 2.0 wt. % |
| HFA134A | 77.7 wt. % |

The solution is produced in the usual way by mixing the individual ingredients together.

| D) Inhalable powder | |
| --- | --- |
| active substance of formula 1 | 80 μg |
| lactose monohydrate ad | 10 mg |

The powder for inhalation is produced in the usual way by mixing the individual ingredients together.

What is claimed is:

1. A compound of formula 1,

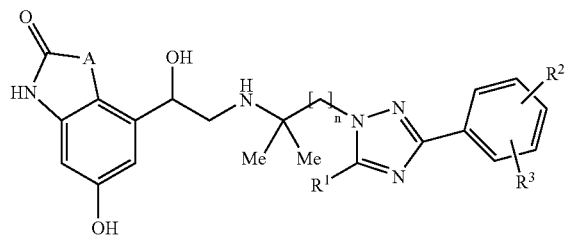

wherein n is 1, 2, 3 or 4;

A is a double-bonded group selected from among —O, —$CR^4R^5$, —$NR^6$, —S, —$CR^4R^5$—O, —$CR^4R^5$—$NR^6$, —CH=CH or —$CH_2$—$CH_2$—;

$R^1$ is —$C_{1-6}$-alkyl;

$R^2$ and $R^3$, which may be identical or different, are H, $C_{1-6}$-alkyl, $C_{2-6}$-alkenyl, $C_{2-6}$-alkynyl, $C_{3-6}$-cycloalkyl, $C_{1-6}$-haloalkyl, —O—$C_{1-6}$-haloalkyl, halogen, OH, CN, $NO_2$, O—$C_{1-6}$-alkyl, —$C_{2-6}$-alkyl-OH, $NH_2$, NH—$C_{1-6}$-alkyl, N($C_{1-6}$-alkyl)$_2$, NHCO—$C_{1-6}$-alkyl, $NHSO_2$—$C_{1-6}$-alkyl, S—$C_{1-6}$-alkyl, SO—$C_{1-6}$-alkyl, $SO_2$—$C_{1-6}$-alkyl, $SO_2NH_2$, $SO_2NH$—$C_{1-6}$-alkyl, $SO_2N$($C_{1-6}$-alkyl)$_2$, $CONH_2$, CONH—$C_{1-6}$-alkyl, CON($C_{1-6}$-alkyl)$_2$, —CO—$C_{1-6}$-alkyl, COOH or COO—$C_{1-4}$-alkyl, or $R^2$ and $R^3$ together are a double-bonded group selected from —O—$CR^4R^5$—O, —O—$CR^4R^5$—$NR^6$ or —CH=CH—CH=CH—;

$R^4$ is H or $C_{1-6}$-alkyl;

$R^5$ is H or $C^{1-6}$-alkyl;

$R^6$ is H or $C^{1-6}$-alkyl, optionally in the form of an individual enantiomer thereof, a mixture of the individual enantiomers or a racemate, optionally in the form of a pharmacologically acceptable acid addition salt thereof, as well as optionally in the form of a hydrate thereof.

2. The compound of formula 1 according to claim 1, wherein n is 1, 2 or 3;

A is a double-bonded group selected from among —$CR^4R^5$—O, —CH=CH or —$CH_2$—$CH_2$;

$R^1$ is —$C_{1-4}$-alkyl;

$R^2$ and $R^3$, which may be identical or different, are H, $C_{1-4}$-alkyl, $C_{2-4}$-alkenyl, $C_{2-4}$-alkynyl, $C_{3-6}$-cycloalkyl, $C_{1-4}$-haloalkyl, —O—$C_{1-4}$-haloalkyl, halogen, OH, CN, $NO_2$, —$C_{2-4}$-alkyl OH, —O—$C_{1-4}$-alkyl, COOH or COO—$C_{1-4}$-alkyl, or $R^2$ and $R^3$ together are a double-bonded group selected from —O—$CR^4R^5$—O, —O—$CR^4R^5$—$NR^6$ or —CH=CH—CH=CH—;

$R^4$ is H or $C_{1-4}$-alkyl;

$R^5$ is H or $C_{1-4}$-alkyl;

$R^6$ is H or $C_{1-4}$-alkyl.

3. The compound of formula 1 according to claim 2, wherein

A is a double-bonded group selected from among —$CR^4R^5$—O, —CH=CH or —$CH_2$—$CH_2$ where $R^4$ is H, methyl or ethyl;

$R^5$ is H, methyl or ethyl.

4. The compound of formula 1 according to claim 3, wherein R1 is methyl, ethyl or propyl.

5. The compound of formula 1 according to claim 4, wherein $R^2$ is, H methyl, ethyl, propyl, vinyl, allyl, propargyl, cyclopropyl, cyclopentyl, cyclohexyl, —$CH_2Cl$, —$CHCl_2$, —$CCl_3$, —$CH_2F$, —$CHF_2$, —$CF_3$, —$CH_2$—$CH_2Cl$, —$CH_2CHCl_2$, —$CH_2$—$CCl_3$, —$CH_2$—$CH_2F$, —$CH_2$—$CHF_2$, —$CH_2$=$CF_3$, —$CH_2$—$CH_2OH$, fluorine, chlorine, bromine, OH, CN, $NO_2$, methoxy, ethoxy, propoxy, COOH, COO-methyl, COO-ethyl, COO-propyl or COO-butyl;

$R_3$ is methyl, ethyl, propyl, vinyl, allyl, propargyl, cyclopropyl, cyclopentyl, cyclohexyl, —$CH_2Cl$, —$CHCl_2$, —$CCl_3$, —$CH_2F$, —$CHF_2$, —$CF_3$, —$CH_2Cl$, —$CH_2$—$CHCl_2$, —$CH_2$—$CCl_3$, —$CH_2$—$CH_2F$, —$CH_2$—$CHF_2$, —$CH_2$—$CF_3$, —$CH_2$—$CH_2OH$, fluorine, chlorine, bromine, OH, CN, $NO_2$, methoxy, ethoxy, propoxy, COOH, COO-methyl, COO-ethyl, COO-propyl or COO-butyl, or $R^2$ and $R^3$ together are a double-bonded group selected from —O—$CR^4R^5$—O, —O—$CR^4R^5$—$NR^6$ or —CH=CH—CH=CH—;

$R^4$ is H, methyl or ethyl;

$R^5$ is H, methyl or ethyl;

$R^6$ is H, methyl or ethyl.

6. The compound of formula 1 according to claim 1, wherein said compound is in the form of an acid addition salt thereof with a pharmacologically acceptable acid which is selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate.

7. The compound of formula 1 according to claim 1, wherein said compound is in the form of the R-enantiomers of formula R-1

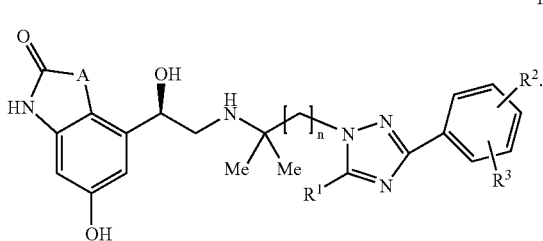

8. A pharmaceutical formulation comprising a compound of formula 1 according to claim 1 together with a pharmaceutically acceptable carrier or excipient.

9. The compound of formula 1 according to claim 2, wherein
n is 2;
A is a double-bonded group selected from among —CR⁴R⁵—O, —CH=CH or —CH₂—CH₂;
R¹ is —C₁₋₄-alkyl;
R² and R³, which may be identical or different, are H, C₁₋₄-alkyl, C₂₋₄-alkenyl, C₂₋₄-alkynyl, C₃₋₆-cycloalkyl, C₁₋₄-haloalkyl, —O—C₁₋₄-haloalkyl, halogen, OH, CN, NO₂, —C₂₋₄-alkyl—OH, —O—C₁₋₄-alkyl, COOH or COO—C₁₋₄-alkyl, or
R² and R³ together are a double-bonded group selected from —O—CR⁴R⁵—O, —O—CR⁴R⁵—NR⁶ or —CH=CH—CH=CH—;
R⁴ is H or C₁₋₄-alkyl;
R⁵ is H or C₁₋₄-alkyl;
R⁶ is H or C₁₋₄-alkyl.

10. The compound of formula 1 according to claim 2, wherein
n is 1, 2 or 3;
A is —CR⁴R⁵—O;
R¹ is —C₁₋₄-alkyl;
R² and R³, which may be identical or different, are H, C₁₋₄-alkyl, C₂₋₄-alkenyl, C₂₋₄-alkynyl, C₃₋₆-cycloalkyl, C₁₋₄-haloalkyl, —O—C₁₋₄-haloalkyl, halogen, OH, CN, NO₂, —C₂₋₄-alkyl OH, —O—C₁₋₄-alkyl, COOH or COO—C₁₋₄-alkyl, or
R² and R³ together are a double-bonded group selected from —O—CR⁴R⁵—O, —O—CR⁴R⁵—NR⁶ or —CH=CH—CH=CH—;
R⁴ is H or C₁₋₄-alkyl;
R⁵ is H or C₁₋₄-alkyl;
R⁶ is H or C₁₋₄-alkyl.

11. The compound of formula 1 according to claim 3, wherein
A is —CR⁴R⁵—O— where
R⁴ is H or methyl;
R⁵ is H, methyl or ethyl.

12. The compound of formula 1 according to claim 3, wherein
A is —CR⁴R⁵—O— where
R⁴ is H;
R⁵ is H, methyl or ethyl.

13. The compound of formula 1 according to claim 3, wherein
A is —CR⁴R⁵—O— where
R⁴ is H, methyl or ethyl;
R⁵ is H or methyl.

14. The compound of formula 1 according to claim 3, wherein
A is —CR⁴R⁵—O— where
R⁴ is H, methyl or methyl;
R⁵ is H.

15. The compound of formula 1 according to claim 5, wherein
R² is H, methyl, ethyl, propyl, vinyl, allyl, propargyl, cyclopropyl, cyclopentyl, cyclohexyl, —CH₂Cl, —CHCl₂, —CCl₃, —CH₂F, —CHF₂, —CF₃, —CH₂—CH₂Cl, —CH₂—CHCl₂, —CH₂—CCl₃, —CH₂—CH₂F, —CH₂—CHF₂, —CH₂—CF₃, —CH₂—CH₂—OH, fluorine, chlorine, bromine, OH, CN, NO₂, methoxy, ethoxy, propoxy, COOH, COO-methyl, COO-ethyl, COO-propyl or COO-butyl;
R³ is methyl, ethyl, propyl, vinyl, allyl, propargyl, cyclopropyl, cyclopentyl, cyclohexyl, —CH₂Cl, —CHCl₂, —CCl₃, —CH₂F, —CHF₂, —CF₃, —CH₂Cl, —CH₂—CHCl₂, —CH₂—CCl₃, —CH₂—CH₂F, —CH₂—CHF₂, —CH₂—CF₃, —CH₂—CH₂OH, fluorine, chlorine, bromine, OH, CN, NO₂, methoxy, ethoxy, propoxy, COOH, COO-methyl, COO-ethyl, COO-propyl or COO-butyl, or
R² and R³ together are a double-bonded group selected from —O—CR⁴R⁵—O, —O—CR⁴R⁵—NR⁶ or —CH=CH—CH=CH—;
R⁴ is H or methyl;
R⁵ is H, methyl or ethyl;
R⁶ is H, methyl or ethyl.

16. The compound of formula 1 according to claim 5, wherein
R² is H, methyl, ethyl, propyl, vinyl, allyl, propargyl, cyclopropyl, cyclopentyl, cyclohexyl, —CH₂Cl, —CHCl₂, —CCl₃, —CH₂F, —CHF₂, —CF₃, —CH₂—CH₂Cl, —CH₂—CHCl₂, —CH₂—CCl₃, —CH₂—CH₂F, —CH₂—CHF₂, —CH₂—CF₃, —CH₂—CH₂OH, fluorine, chlorine, bromine, OH, CN, NO₂, methoxy, ethoxy, propoxy, COOH, COO-methyl, COO-ethyl, COO-propyl or COO-butyl;
R₃ is methyl, ethyl, propyl, vinyl, allyl, propargyl, cyclopropyl, cyclopentyl, cyclohexyl, —CH₂Cl, —CHCl₂, —CCl₃, —CH₂F, —CHF₂, —CF₃, —CH₂Cl, —CH₂—CHCl₂, —CH₂—CCl₃, —CH₂—CH₂F, —CH₂—CHF₂, —CH₂—CF₃, —CH₂—CH₂OH, fluorine, chlorine, bromine, OH, CN, NO₂, methoxy, ethoxy, propoxy, COOH, COO-methyl, COO-ethyl, COO-propyl or COO-butyl, or
R² and R³ together are a double-bonded group selected from —O—CR⁴R⁵—O, —O—CR⁴R⁵—NR⁶ or —CH=CH—CH=CH—;
R⁴ is H;
R⁵ is H, methyl or ethyl;
R⁶ is H, methyl or ethyl.

17. The compound of formula 1 according to claim 5, wherein
R² is H, methyl, ethyl, propyl, vinyl, allyl, propargyl, cyclopropyl, cyclopentyl, cyclohexyl, —CH₂Cl, —CHCl₂, —CCl₃, —CH₂F, —CHF₂, —CF₃, —CH₂—CH₂Cl, —CH₂—CHCl₂, —CH₂—CCl₃, —CH₂—CH₂F, —CH₂—CHF₂, —CH₂—CF₃, —CH₂—CH₂OH, fluorine, chlorine, bromine, OH, CN, NO₂, methoxy, ethoxy, propoxy, COOH, COO-methyl, COO-ethyl, COO-propyl or COO-butyl;
R³ is methyl, ethyl, propyl, vinyl, allyl, propargyl, cyclopropyl, cyclopentyl, cyclohexyl, —CH₂—Cl, —CHCl₂, —CCl₃, —CH₂F, —CHF₂, —CF₃, —CH₂Cl, —CH₂—CHCl₂, —CH₂—CCl₃, —CH₂—CH₂F, —CH₂—CHF₂, —CH₂—CF₃, —CH₂—CH₂OH, fluorine, chlorine, bromine, OH, CN, NO$_2$, methoxy, ethoxy, propoxy, COOH, COO-methyl, COO-ethyl, COO-propyl or COO-butyl, or R$^2$ and R$^3$ together are a double-bonded group selected from —O—CR$^4$R$^5$—O, —O—CR$^4$R$^5$—NR$^6$ or —CH=CH—CH=CH—;

R$^4$ is H, methyl or ethyl;
R$^5$ is H or methyl;
R$^6$ is H, methyl or ethyl.

18. The compound of formula 1 according to claim 5, wherein

R$^2$ is H methyl, ethyl, propyl, vinyl, allyl, propargyl, cyclopropyl, cyclopentyl, cyclohexyl, —CH$_2$Cl, —CHCl$_2$, —CCl$_3$, —CH$_2$F, —CHF$_2$, —CF$_3$, —CH$_2$—CH$_2$Cl, —CH$_2$—CHCl$_2$, —CH$_2$—CCl$_3$, —CH$_2$—CH$_2$F, —CH$_2$—CHF$_2$, —CH$_2$—CF$_3$, —CH$_2$—CH$_2$OH, fluorine, chlorine, bromine, OH, CN, NO$_2$, methoxy, ethoxy, propoxy, COOH, COO-methyl, COO-ethyl, COO-propyl or COO-butyl;

R$^3$ is methyl, ethyl, propyl, vinyl, allyl, propargyl, cyclopropyl, cyclopentyl, cyclopentyl, cyclohexyl, —CH$_2$—Cl, —CHCl$_2$, —CCl$_3$, —CH$_2$F, —CHF$_2$, —CF$_3$, —CH$_2$—CH$_2$Cl, —CH$_2$—CHCl$_2$, —CH$_2$—CCl$_3$, —CH$_2$—CH$_2$F, —CH$_2$—CHF$_2$, —CH$_2$—CF$_3$, —CH$_2$—CH$_2$OH, fluorine, chlorine, bromine, OH, CN, NO$_2$, methoxy, ethoxy, propoxy, COOH, COO-methyl, COO-ethyl, COO-propyl or COO-butyl, or R$^2$ and R$^3$ together are a double-bonded group selected from —O—CR$^4$R$^5$—O, —O—CR$^4$R$^5$—NR$^6$ or —CH=CH—CH=CH—;

R$^4$ is H, methyl or ethyl;
R$^5$ is H;
R$^6$ is H, methyl or ethyl.

19. The compound of formula 1 according to claim 5, wherein

R$^2$ is H, methyl, ethyl, propyl, vinyl, allyl, propargyl, cyclopropyl, cyclopentyl, cyclohexyl, —CH$_2$Cl, —CHCl$_2$, —CCl$_3$, —CH$_2$F, —CHF$_2$, —CF$_3$, —CH$_2$—CH$_2$Cl, —CH$_2$—CHCl$_2$, —CH$_2$—CCl$_3$, —CH$_2$—CH$_2$F, —CH$_2$—CHF$_2$, —CH$_2$—CF$_3$, —CH$_2$—CH$_2$—OH, fluorine, chlorine, bromine, OH, CN, NO$_2$, methoxy, ethoxy, propoxy, COOH, COO-methyl, COO-ethyl, COO-propyl or COO-butyl;

R$^3$ is methyl, ethyl, propyl, vinyl, allyl, propargyl, cyclopropyl, cyclopentyl, cyclohexyl, —CH$_2$Cl, —CHCl$_2$, —CCl$_3$, —CH$_2$F, —CHF$_2$, —CF$_3$, —CH$_2$Cl, —CH$_2$—CHCl$_2$, —CH$_2$—CCl$_3$, —CH$_2$—CH$_2$F, —CH$_2$—CHF$_2$, —CH$_2$—CF$_3$, —CH$_2$—CH$_2$OH, fluorine, chlorine, bromine, OH, CN, NO$_2$, methoxy, ethoxy, propoxy, COOH, COO-methyl, COO-ethyl, COO-propyl or COO-butyl, or R$^2$ and R$^3$ together are a double-bonded group selected from —O—CR$^4$R$^5$—O, —O—CR$^4$R$^5$—NR$^6$ or —CH=CH—CH=CH—;

R$^4$ is H, methyl or ethyl;
R$^5$ is H, methyl or ethyl;
R$^6$ is H or methyl.

20. The compound of formula 1 according to claim 5, wherein

R$^2$ is H, methyl, ethyl, propyl, vinyl, allyl, propargyl, cyclopropyl, cyclopentyl, cyclohexyl, —CH$_2$Cl, —CHCl$_2$, —CCl$_3$, —CH$_2$F, —CHF$_2$, —CF$_3$, —CH$_2$—CH$_2$Cl, —CH$_2$—CHCl$_2$, —CH$_2$—CCl$_3$, —CH$_2$—CH$_2$F, —CH$_2$—CHF$_2$, —CH$_2$—CF$_3$, —CH$_2$—CH$_2$OH, fluorine, chlorine, bromine, OH, CN, NO$_2$, methoxy, ethoxy, propoxy, COOH, COO-methyl, COO-ethyl, COO-propyl or COO-butyl;

R$^3$ is methyl, ethyl, propyl, vinyl, allyl, propargyl, cyclopropyl, cyclopentyl, cyclohexyl, —CH$_2$Cl, —CHCl$_2$, —CCl$_3$, —CH$_2$F, —CHF$_2$, —CF$_3$, —CH$_2$Cl, —CH$_2$—CHCl$_2$, —CH$_2$—CCl$_3$, —CH$_2$—CHF$_2$, —CH$_2$—CF$_3$, —CH$_2$—CH$_2$OH, fluorine, chlorine, bromine, OH, CN, NO$_2$, methoxy, ethoxy, propoxy, COOH, COO-methyl, COO-ethyl, COO-propyl or COO-butyl, or R$^2$ and R$^3$ together are a double-bonded group selected from —O—CR$^4$R$^5$—O, —O—CR$^4$R$^5$—NR$^6$ or —CH=CH—CH=CH—;

R$^4$ is H, methyl or ethyl;
R$^5$ is H, methyl or ethyl;
R$^6$ is H.

* * * * *